(12) United States Patent
Che et al.

(10) Patent No.: US 10,247,693 B2
(45) Date of Patent: *Apr. 2, 2019

(54) DISPOSABLE TEST SENSOR WITH IMPROVED SAMPLING ENTRANCE

(71) Applicant: Changsha Sinocare Inc., Changsha (CN)

(72) Inventors: Hongli Che, Changsha (CN); Shaobo Li, Changsha (CN)

(73) Assignee: Changsha Sinocare Inc., Changsha, Hunan (CN)

( * ) Notice: Subject to any disclaimer, the term of this patent is extended or adjusted under 35 U.S.C. 154(b) by 51 days.

This patent is subject to a terminal disclaimer.

(21) Appl. No.: 15/345,791

(22) Filed: Nov. 8, 2016

(65) Prior Publication Data

US 2017/0052139 A1 Feb. 23, 2017

Related U.S. Application Data

(63) Continuation of application No. 13/890,303, filed on May 9, 2013, now Pat. No. 9,523,653.

(51) Int. Cl.
*G01N 27/327* (2006.01)
*C12Q 1/00* (2006.01)

(52) U.S. Cl.
CPC ......... *G01N 27/3272* (2013.01); *C12Q 1/006* (2013.01); *Y10T 29/49117* (2015.01)

(58) Field of Classification Search
CPC .................................................. G01N 27/3272
See application file for complete search history.

(56) References Cited

U.S. PATENT DOCUMENTS

| 4,431,507 A | 2/1984 | Nankai et al. |
| 4,498,968 A | 2/1985 | Yamada et al. |
| 4,534,356 A | 8/1985 | Papadakis |

(Continued)

FOREIGN PATENT DOCUMENTS

| JP | 2000-162176 A | * 6/2000 | ........... G01N 27/416 |
| WO | WO 2013117924 | 8/2013 | |

(Continued)

OTHER PUBLICATIONS

JPO computer-generated English language translation of Nakajima JP 2000-162176 A . Patent published Jun. 16, 2000.*

(Continued)

*Primary Examiner* — Alexander S Noguerola
(74) *Attorney, Agent, or Firm* — Lambert Shortell & Connaughton; Gary E. Lambert; David J. Connaughton, Jr.

(57) ABSTRACT

A disposable electrochemical test sensor designed to facilitate sampling of fluid samples. It has a fluid chamber having a novel extra wide sampling entrance, but no additional air escape vent. The chamber provides a reservoir from which a sample fluid can be drawn into the chamber through capillary action. The sampling entrance provided can draw fluid into the chamber through any part of the opening, allowing easy targeting the samples with small volume, picking up smeared samples, and added tolerance to users who jam the tip of the sensor into users' finger. The sampling entrance also serves as air escape vent. Such one opening sensor alleviates over-flow issue often encountered in convenient sensors.

18 Claims, 9 Drawing Sheets

(56) References Cited

U.S. PATENT DOCUMENTS

| | | | |
|---|---|---|---|
| 5,102,525 A | 4/1992 | Miyahara et al. | |
| 5,120,420 A | 6/1992 | Nankai et al. | |
| 5,126,034 A | 6/1992 | Carter et al. | |
| 5,128,012 A | 7/1992 | Szuminsky et al. | |
| 5,128,015 A | 7/1992 | Szuminsky et al. | |
| 5,138,521 A | 8/1992 | Koshishi | |
| 5,264,103 A | 11/1993 | Yoshioka et al. | |
| 5,344,545 A | 9/1994 | Tsukada et al. | |
| 5,437,999 A | 8/1995 | Diebold et al. | |
| 5,575,895 A | 11/1996 | Ikeda et al. | |
| 5,582,697 A | 12/1996 | Ikeda et al. | |
| 5,665,222 A | 9/1997 | Heller et al. | |
| 5,708,247 A | 1/1998 | McAleer et al. | |
| 5,739,039 A | 4/1998 | Hugues | |
| 5,762,770 A | 6/1998 | Pritchard et al. | |
| 5,858,201 A | 1/1999 | Otsuka et al. | |
| 5,975,153 A | 11/1999 | Hill et al. | |
| 6,004,441 A | 12/1999 | Fujiwara et al. | |
| 6,071,391 A * | 6/2000 | Gotoh | C12Q 1/005 204/403.05 |
| 6,125,292 A | 9/2000 | Uenoyama et al. | |
| 6,287,451 B1 | 9/2001 | Winarta et al. | |
| 6,428,664 B1 | 8/2002 | Bhullar et al. | |
| 6,540,891 B1 | 4/2003 | Stewart et al. | |
| 6,592,746 B1 | 7/2003 | Feldman et al. | |
| 6,645,359 B1 | 11/2003 | Bhullar et al. | |
| 6,767,440 B1 | 7/2004 | Bhullar et al. | |
| 6,767,441 B1 * | 7/2004 | Cai | C12Q 1/004 204/403.03 |
| 6,787,013 B2 | 9/2004 | Chang et al. | |
| 6,803,205 B2 | 10/2004 | Duffy et al. | |
| 6,923,894 B2 | 8/2005 | Huang et al. | |
| 6,942,770 B2 | 9/2005 | Cai et al. | |
| 7,063,776 B2 | 6/2006 | Huang | |
| 7,073,246 B2 | 7/2006 | Bhullar et al. | |
| 7,118,667 B2 | 10/2006 | Lee | |
| 7,276,146 B2 | 10/2007 | Wilsey | |
| 7,288,174 B2 | 10/2007 | Cui et al. | |
| 7,297,248 B2 | 11/2007 | Bae et al. | |
| 7,386,937 B2 | 6/2008 | Bhullar et al. | |
| 7,547,383 B2 | 6/2009 | Cai et al. | |
| 7,641,785 B2 | 1/2010 | Shinno et al. | |
| RE41,264 E | 4/2010 | Cai et al. | |
| 7,740,746 B2 | 6/2010 | Huang | |
| 7,802,467 B2 | 9/2010 | Wang | |
| 7,824,616 B2 | 11/2010 | Katsuki | |
| 78,245,616 | 11/2010 | Katsuki et al. | |
| 7,955,484 B2 | 6/2011 | Cai et al. | |
| RE42,567 E | 7/2011 | Hodges et al. | |
| RE42,953 E | 11/2011 | Crismore et al. | |
| 8,088,271 B2 | 1/2012 | Fujiwara et al. | |
| 8,128,981 B2 | 3/2012 | Popovich et al. | |
| 8,142,629 B2 | 3/2012 | Miyazaki et al. | |
| 8,211,379 B2 | 7/2012 | Burke et al. | |
| 8,222,044 B2 | 7/2012 | Bhullar et al. | |
| 8,287,703 B2 | 10/2012 | Bhullar et al. | |
| RE43,815 E | 11/2012 | Crismore et al. | |
| 8,303,801 B2 | 11/2012 | Wilsey | |
| 8,414,761 B2 | 4/2013 | Gotoh et al. | |
| 8,430,999 B2 | 4/2013 | Onoda et al. | |
| 8,480,869 B2 | 7/2013 | Fujiwara et al. | |
| 8,535,497 B2 | 9/2013 | Fujiwara et al. | |
| 8,540,864 B2 | 9/2013 | Fujiwara et al. | |
| 8,551,308 B2 | 10/2013 | Bhullar et al. | |
| 8,679,309 B2 | 3/2014 | Beer et al. | |
| 9,523,653 B2 * | 12/2016 | Che | G01N 27/3272 |
| 2001/0034068 A1 | 10/2001 | Spivey et al. | |
| 2004/0050717 A1 | 3/2004 | Teodorczyk et al. | |
| 2004/0256228 A1 * | 12/2004 | Huang | G01N 33/5438 204/434 |
| 2005/0145490 A1 | 7/2005 | Shinno et al. | |
| 2005/0214171 A1 | 9/2005 | Gerstle et al. | |
| 2005/0269214 A1 | 12/2005 | Lee | |
| 2005/0277850 A1 | 12/2005 | Mace et al. | |
| 2007/0131548 A1 | 6/2007 | Winarta et al. | |
| 2007/0235347 A1 | 10/2007 | Chatelier et al. | |
| 2008/0006530 A1 | 1/2008 | Winarta et al. | |
| 2008/0128278 A1 | 6/2008 | Bae et al. | |
| 2008/0148873 A1 | 6/2008 | Wang | |
| 2009/0078030 A1 | 3/2009 | Jung | |
| 2009/0157001 A1 | 6/2009 | Jones | |
| 2009/0215159 A1 | 8/2009 | Kirby | |
| 2011/0048940 A1 | 3/2011 | Wang et al. | |
| 2011/0174613 A1 | 7/2011 | Miyazaki et al. | |
| 2012/0174688 A1 | 7/2012 | Calasso et al. | |
| 2012/0186996 A1 | 7/2012 | Wilsey et al. | |
| 2012/0234487 A1 | 9/2012 | Wang | |
| 2013/0062221 A1 | 3/2013 | Cai et al. | |
| 2013/0306472 A1 | 11/2013 | Kaneda et al. | |
| 2013/0341208 A1 | 12/2013 | Whyte et al. | |
| 2014/0021046 A1 | 1/2014 | Huang et al. | |
| 2014/0054171 A1 | 2/2014 | Feldman et al. | |
| 2014/0147912 A1 | 5/2014 | Cho et al. | |
| 2014/0158553 A1 | 6/2014 | Fujiwara et al. | |
| 2014/0174922 A1 | 6/2014 | Beer et al. | |
| 2014/0262773 A1 | 9/2014 | Riggles et al. | |

FOREIGN PATENT DOCUMENTS

| | | |
|---|---|---|
| WO | WO 2013190072 | 12/2013 |
| WO | WO 2014140161 | 9/2014 |

OTHER PUBLICATIONS

USPTO Office Action—U.S. Appl. No. 14/099,418, dated Mar. 23, 2016.

USPTO Office Action—U.S. Appl. No. 14/153,654, dated Jun. 14, 2016.

USPTO Office Action—U.S. Appl. No. 14/184,764, dated Jul. 1, 2016.

Patent Cooperation Treaty International Search Report—WO2015126456-ISR-010, dated Dec. 22, 2014.

Patent Cooperation Treaty International Search Report—WO2015084448, dated Dec. 22, 2014.

Patent Cooperation Treaty International Search Report—WO2015105536, dated Dec. 22, 2014.

Factors Affecting Blood Glucose Monitoring: Sources of Errors in Measurement, Barry H. Ginsberg, J Diabetes Sci. Technol. Jul. 2009; 3(4): 903-913.

* cited by examiner

DISPOSABLE TEST SENSOR WITH IMPROVED SAMPLING ENTRANCE

FIELD OF THE INVENTION

The present invention generally relates to a test sensor or strip. More specifically, the present invention generally relates to a disposable biosensor with a fluid chamber that is adapted to receive a fluid sample around with small volume. Still more specifically, the present invention generally relates an electrochemical biosensor with an extra wide sampling entrance. Still more specifically, the present invention relates methods of making and using the biosensors.

BACKGROUND OF THE INVENTION

The use of disposable test sensors such as strips in the medical field for testing various analytes in body fluid is well known. The accurate determination of analytes in body fluids is of great importance in the diagnoses of certain physiological abnormalities. In particular, it is important that diabetic individuals frequently check their glucose level in their body fluids to regulate the glucose intake in their daily diets. The results of such tests can be used to determine the insulin dosage or other medication needs to be administered. In one type of blood-glucose testing system, test sensors, or called glucose strips, are used by diabetic individuals to test a sample of blood in connection with a hand-held meter. The glucose strips are used by millions of diabetics throughout the world on a daily base.

There are hundreds of brand names of glucose strips in the market. They are very similar in terms of sensor construction: i.e., a channel is formed between a generally U-shaped spacer and is adapted to receive blood from the opening end of the sensor through capillary action and escape air from the other end through an air escape vent. In order to reduce blood volume, thus reduce pain from piercing finger or other sampling points, the blood receiving chamber is usually small and, as a result, the sampling entrance is also relatively small. As the volume of fluid chambers in the sensors decreases, it becomes increasingly more difficult to fill the fluid chamber with the sample to be analyzed. It has been observed that users may abuse the test sensor by jamming the tip of the test sensor into the individual's finger, which very probably results in incomplete blood filling, non-continuous filling or wiggling of blood flow. Additionally, in some existing test sensors, it is difficult to position the fluid sample within the channel entrance opening especially for those diabetics who have poor vision and/or trembling hand. Besides, blood samples turn to smear around the tip of fingers or other sampling points. It becomes very difficult to draw such smeared blood into the sensor chamber. All of these phenomena may eventually lead to biased readings, and as a result, wrong dosage of insulin administration and even life threatening errors may occur.

Therefore, in order to reduce or eliminate such biased readings caused by such user action and/or reduce the difficulty in connection with sampling, it would be highly desirable to have a more user friendly test sensor that could easily target sample, easily draw sample into the sensor chamber, and alleviate incomplete filling, non-continuous filling and other issues that may result in inaccurate test results. The present disclosure is directed to a novel design and method to overcome one or more of the limitations in the prior arts.

SUMMARY OF THE INVENTION

According to the first embodiment, a disposable electrochemical test sensor has a sample chamber having a novel extra wide sampling entrance, but no additional air escape vent. Such a design is adapted to improve sampling of fluid samples. The fluid chamber provides a reservoir from which sample fluid can be drawn into the sample receiving chamber through capillary action. The extra wide sampling entrance provided by the present invention can draw blood into the chamber through any part of the opening end. Thus it allows easily targeting the samples with small volume, picking up smeared samples and alleviating jamming the opening end. The extra wide sampling entrance provided by the present invention also serves as the air escape vent. Such one opening sensor eliminates over-flow issue often encountered in convenient sensors. In preferred embodiments, the sensor consists of multiple layers which include a base layer having conductive coatings serving as working and reference electrodes; a second base layer used to define the electrode areas and hold chemistries; a first upper layer having semi-circular shape serving as spacer; and a second upper layer with a hydrophilic surface facing to the chamber. The upper and base layers are attached through adhesives or other ways to bond each other, such that the fluid chamber is formed between a portion of the lower layer surface and the upper layer surface at one end of the sensor, while the other end of the sensor having conductive layer exposed serve as electric contacts in connection with a monitor or meter.

According to the second embodiment, a disposable electrochemical test sensor has a sample chamber having a novel extra wide sampling entrance, but no additional air escape vent. Such a design is adapted to improve sampling of fluid samples. The chamber provides a reservoir from which sample fluid can be drawn into the sample receiving chamber through capillary action. The extra wide sampling entrance provided by the present invention can draw blood into the fluid chamber through any part of the front opening end, and can also draw blood into the fluid chamber through part of left side and part of right side near the opening end. The front opening and both side openings form a large opening, serving as blood sample entrance. Thus such unique design allows easily targeting the samples with small volume, picking up smeared samples and alleviating jamming of the opening by users' finger. The extra wide sampling entrance provided by the present invention also serves as the air escape vent. That is to say the air escape vent joins to the blood sampling entrance opening. Such two-in-one opening sensor eliminates over-flow issue often encountered in convenient sensors.

In preferred embodiments, the test sensor consists of multiple layers which include a base layer having conductive coatings serving as working and reference electrodes; a second base layer used to define the electrode areas and hold chemistries; a first upper layer having semi-circular shape serving as spacer; and a second upper layer with a hydrophilic surface facing to the chamber. The upper and base layers are attached through adhesives or other ways to bond each other, such that the fluid chamber is formed between a portion of the lower layer surface and the upper layer surface at one end of the sensor, while the other end of the sensor having conductive layers exposed serve as electric contacts in connection with a monitor or meter.

According to one method, an analyte concentration is measured. A disposable electrochemical test sensor is provided having a sample chamber having a novel extra wide sampling entrance, but no additional air escape vent. The chamber provides a reservoir from which sample fluid can be drawn into the sample receiving chamber through capillary action. The extra wide sampling entrance provided by the present invention also serves as the air escape vent. In preferred embodiments, the sensor consists of multiple layers which include a base layer having conductive coatings serving as working and reference electrodes; a second base layer used to define the electrode areas and hold chemistries; a first upper layer serves as spacer which may have different shapes, such as circular arc, square, rectangular, triangle, regular trapezoid, inverted trapezoid; and a second upper layer with a hydrophilic surface facing to the chamber. The upper and base layers are attached through adhesives or other ways to bond each other, such that the fluid chamber is formed between a portion of the lower layer surface and the upper layer surface at one end of the sensor, while the other end of the sensor having conductive layers exposed serve as electric contacts in connection with a monitor or meter.

DETAILED DESCRIPTION OF ILLUSTRATED EMBODIMENTS

The test sensor of the present invention is directed to improve sampling entrance of the strip for the determination of an analyte concentration of in a fluid sample, such as blood. In one embodiment, a test sensor is adapted to receive a fluid sample from one end of the sensor, while the other end is connected with an instrument or meter. Analytes that may be measured include, but not limited to glucose, lactate, uric acid, creatinine, creatine, cholesterol, triglycerides, hemoglobin, bilirubin, alcohol, etc. The fluid sample may be any body fluid, thus, the analytes may be in, for example, a whole blood sample, a blood serum sample, a blood plasma sample, other body fluids like tears, interstitial fluid and urine. In one preferred method, the testing equipment is a hand-held meter.

In a particular embodiment, the sensor comprises multiple layers which include a base layer having conductive coatings serving as working and reference electrodes; a second base layer used to define the electrode areas and hold chemistries; a first upper layer having semi-circular shape serving as a spacer; and a second upper layer with a hydrophilic surface facing to the chamber. The upper and base layers are attached such that the fluid chamber is formed between a portion of the lower layer surface and the upper layer surface at one end of the sensor, while the other end of the sensor having conductive layers exposed serves as electric contacts.

Figure 1:
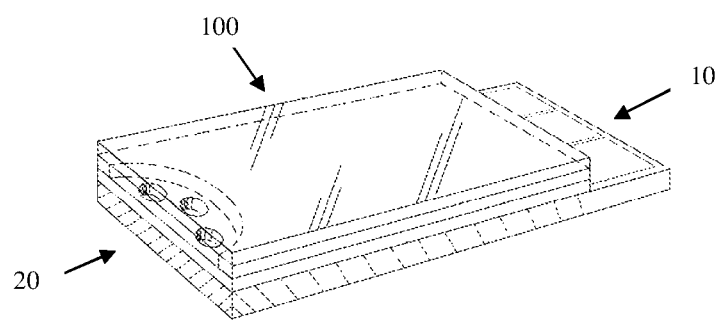
FIG. 1 is a perspective view of the test sensor of the present invention.
Figure 2:
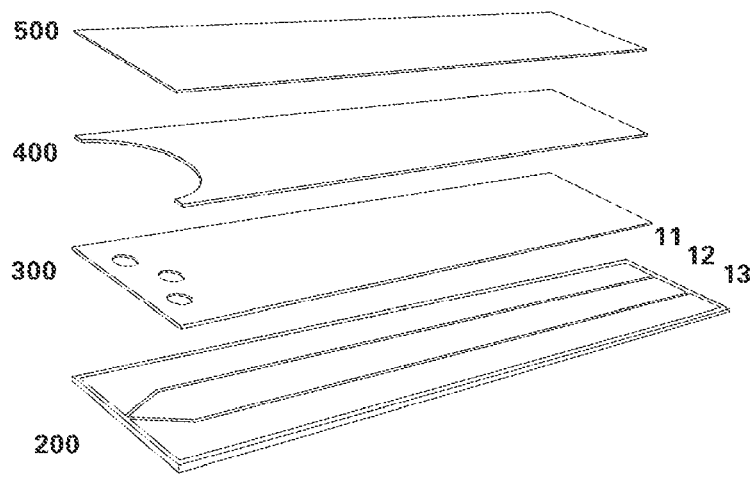
FIG. 2 is an exploded view of the test sensor of the present invention showing the four component layers.
Figure 3:
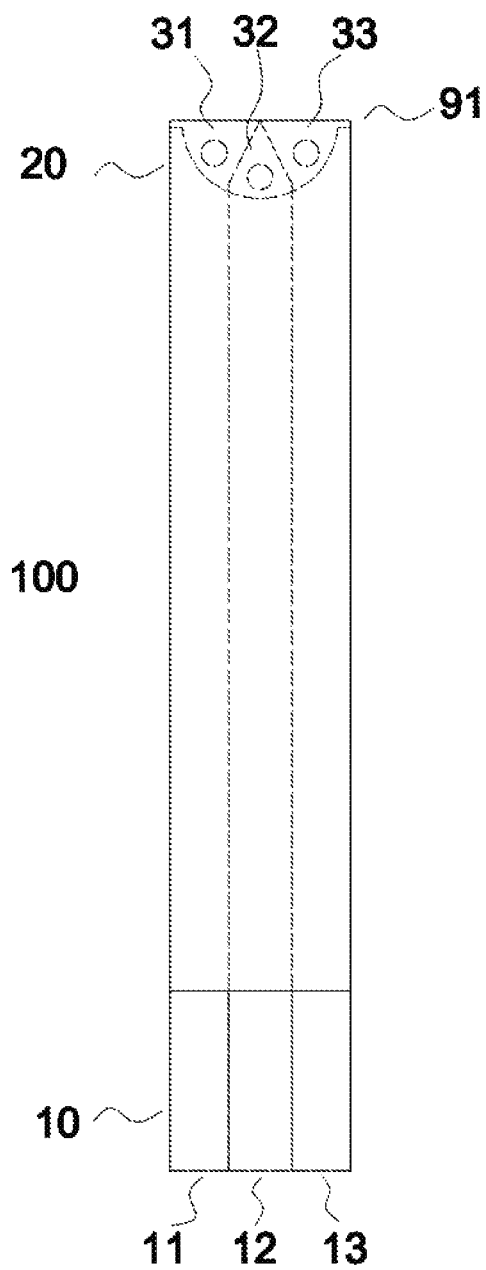
FIG. 3 is a top view of the test sensor of the present invention consisting of four laminated layers according to one embodiment.

In one embodiment, the test sensor is an electrochemical test sensor. FIG. 1 shows a perspective view of the test sensor of the present invention. The sensor has a sensor body 100, an electric contact end 10 and sampling end 20. The electric contact end may have at least two contacts used for one working electrode and one reference electrode, respectively. In one preferred embodiment, the electric contact end has three electric contacts serving as contacts for a first working electrode 11; a second working electrode 13 and a reference electrode 12, respectively. In one embodiment, the test sensor consists of multiple layers which include a first base layer 200; a second base layer 300; a first upper layer 400; and a second upper layer 500, as shown in FIG. 2. FIG. 3 shows a top view of the test sensor consisting of four laminated layers according to one embodiment.

Figure 4:
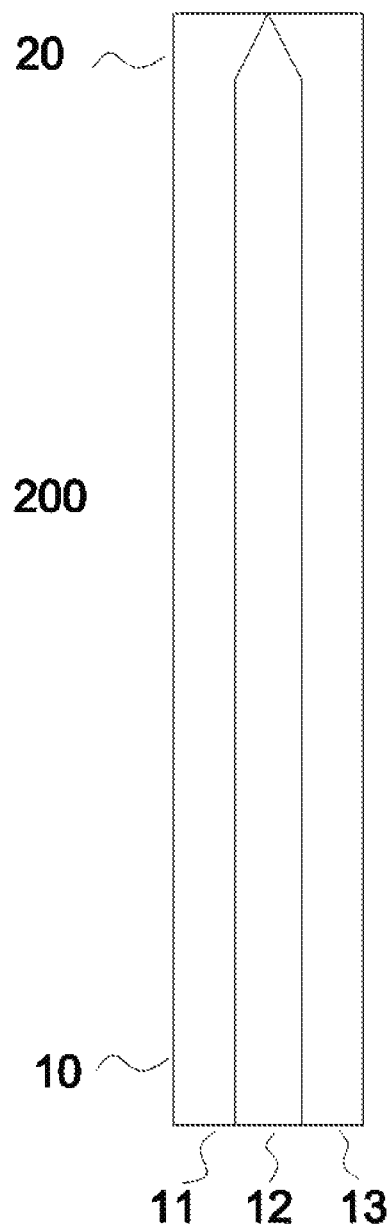
FIG. 4 is a top view of a first base layer to be used in forming a test sensor according to one embodiment.

FIG. 4 shows a top view of a first base layer 200 to be used in forming a test sensor according to one embodiment. The first base layer 200 may be made from a variety of materials such as polymeric materials, coated with conductive materials such as carbon, various metals or metal oxides. The first base layer 200 with conductive coating serves as substrate of the test sensor and chamber forming layer. It also serves as electrodes at one end 20 and electric contacts at the other end 10. Non-limiting examples of polymeric materials, that may be used to form the base layer include, but not limited to polyethylene, polypropylene, polystyrene, polyvinyl chloride, and polytetrafluoroethylene, polycarbonate, polyethylene terephthalate, polyethylene naphthalate, polyimide and combinations thereof. The conductive coating may be formed by a variety of methods which are well known in the field including, but not limited to printing (e.g., screen-printing), coating (e.g., reverse roll), vapor deposition, sputtering, chemical deposition, and electrochemical deposition. The conductive coating may be on a whole piece of insulating material. If so, a desired number of electric conduits must be made. This can be achieved by etching/scribing the required number of conductive conduits. The etching process may be accomplished chemically, by mechanically scribing lines in the conductive layer, or by using a laser to scribe the conductive layer into separate conductive conduits. The conductive materials may be, but not limited to various carbon materials; various noble metals like gold, platinum, palladium, iridium, rhodium, ruthenium; various metal oxides like indium oxide, tin oxide; and combinations thereof.

Figure 5:
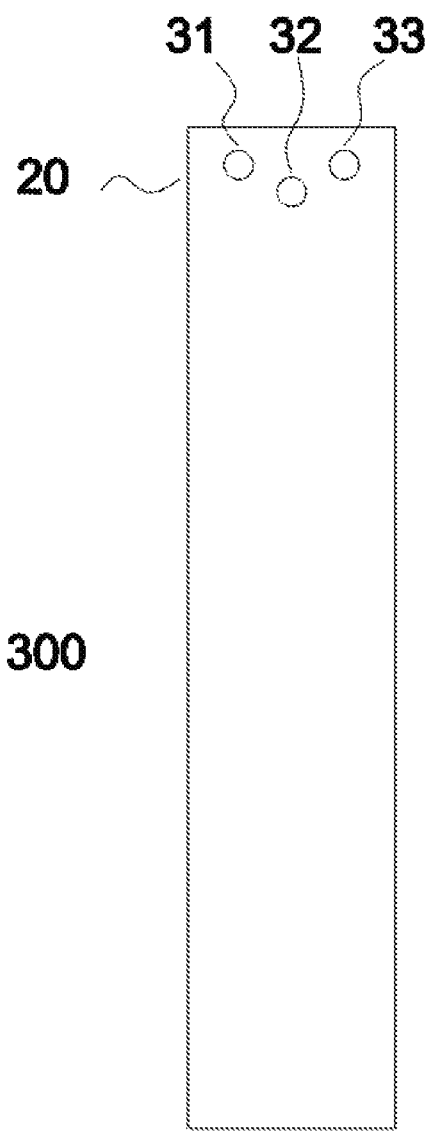
FIG. 5 is a top view of the second base layer to be used in forming a test sensor according to one embodiment.

FIG. 5 shows a top view of the second base layer to be used in forming a test sensor according to one embodiment. The second base layer 300 virtually has same width as the first base layer 200, but shorter in length at the end 10 to expose electric contacts. The second base layer 300 is made of electric insulating layer and it is shorter than the first base layer at the electric contact end 10 so that conductive coating at the first base layer can be exposed for electric contacts when connected with test monitoring device like a hand-held meter. The second base layer 300 has at least one cutout at the end 20. The cutout exposes a part of the conductive layer when laminated with the first base layer 200 and thus defines the electrode area. The cutout can also hold chemistries within the well formed. In one embodiment, the second base layer 300 has at least two such cutouts. In one preferred embodiment, the second base layer 300 has three round cutouts (31, 32, 33) at the end 20 serving as a first working electrode 31; a reference electrode 32 and a second working electrode 33. These cutouts have a diameter ranging from 0.1 mm to 2.5 mm. Preferably, the diameter is ranging from 0.5 mm to 1.5 mm. More preferably, it is around 1 mm. The electrode cutouts 31, 32, 33 have a certain depth, which depends on the thickness of the electric insulating materials used, thus form three wells and can hold chemistries within the wells. Preferably, the thickness of the electric insulating materials is from 0.01 mm to 0.2 mm. More preferably it is around 0.05 mm. In one embodiment of the present invention, the electrode cutouts 31, 32, 33 in the second base layer 300 have the same shape and dimensions. But they can have different shapes, dimensions and/or arrangement orders, without deviating from the scope and spirit of the present invention. The placement of all of the cutouts is such that they will be all positioned within the sample fluid chamber described above. The cutouts may be made by die cutting the insulating material mechanically, or cutting with a laser, and then fastening the material to the first base layer. An adhesive, such as a pressure-sensitive adhesive, may be used to secure the second base insulating layer 300 to the first base layer 200. Adhesion may also be accomplished by ultrasonically bonding the second base layer 300 to the first base layer 200. The second base layer 300 may also be made by screen printing an insulating material, by binding a photopolymer or by heat-sealing an insulating material over the first base layer 200.

Figure 6:
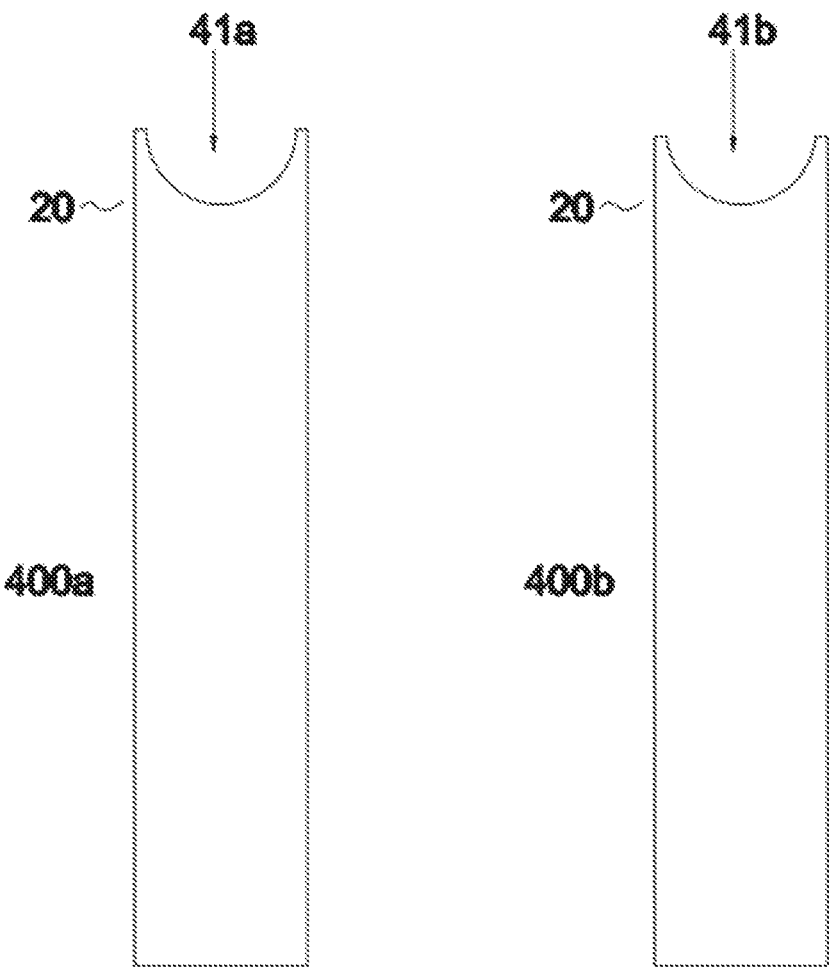
FIG. 6a is a top view of the first upper layer to be used in forming a test sensor according to the first embodiment.
FIG. 6b is a top view of the first upper layer to be used in forming a test sensor according to the second embodiment.

FIG. 6a shows a top view of the first upper layer 400a to be used in forming a test sensor according to the first embodiment. The first upper layer 400a virtually has same width and length as the second base layer 300. The first upper layer 400a serves as a spacer in between the two base layers 200/300 and the second upper layer 500. The first upper layer 400a, or spacer, is also made of a plastic insulating material with glue or adhesive on both sides and creates the sample fluid chamber of the laminated body (FIGS. 1-3). It contains a semi-circular shaped cutout 41a at the end 20 which overlays the second base layer 300 with the open end corresponding to the open end of the laminated body described earlier. The semi-circular shaped cutout 41a has a diameter of at least 1 mm. The diameter can be larger than or equal to the width of the first base layer 200 or second base layer 300. Preferably, it is slightly smaller than the width of the second base layer 300. More preferably, it is around 2 mm to 20 mm in the present invention. Assuming the test sensor or the component layers (200, 300, 400a and 500) in the present invention have a width of around 6 mm, preferably, the diameter of the semi-circular shaped cutout is around 5.2 mm. Thus, a blood sample can enter the fluid chamber from any part of the entire opening end. A double coated, pressure-sensitive adhesive tape may be used as the first upper layer 400a. The cutout 41a creating the fluid chamber may have different shapes, including, but not limited to semi-circular, circular arc, square, rectangular, triangle, regular trapezoid, inverted trapezoid and etc. In one preferred embodiment, the cutout is in semi-circular shape. Obviously, the thickness and size of the cutout 41a determine the volume of the capillary chamber. Preferably, the first upper layer 400a has a thickness ranging from 0.01 mm to 0.5 mm, thus, the volume of the fluid chamber is about 0.1 to 5 microliter in the present invention.

FIG. 6b shows a top view of the first upper layer 400b to be used in forming a test sensor according to the second embodiment. The first upper layer 400b is alternative to the first upper layer 400a. The first upper layer 400b also serves as a spacer in between the two base layers 200/300 and the second upper layer 500. The first upper layer 400b virtually has same width as the first upper layer 400a, but it is slightly shorter in length at the end 20, as a result, leaving openings at both corners after all four component layers 200, 300, 400b and 500 are laminated. Such a unique design of the present invention forms an over 180° sampling entrance, even wider opening compared to the first embodiment described above. Therefore, a blood sample not only enters the fluid chamber from any part of the front opening, but also from both side opening of the test sensor at the end 20. The first upper layer 400b, or spacer, is also made of a plastic insulating material with glue or adhesive on both sides and creates the sample fluid chamber of the laminated body. It contains a semi-circular shaped cutout 41b on the end 20 which overlays the second base layer 300 with the open end corresponding to the open end of the laminated body described earlier. The semi-circular shaped cutout 41b has a diameter of at least 1 mm. The diameter can be larger than or equal to the width of the second base layer 300. Preferably, it is slightly smaller than the width of the second base layer 300. More preferably, it is around 2 mm to 20 mm. Assuming the test sensor or the component layers (200, 300, 400a and 500) in the present invention has a width of around 6 mm, preferably, the diameter of the semi-circular shaped cutout is around 5.2 mm. A double coated, pressure-sensitive adhesive tape may be used as the first upper layer 400b. The cutout 41b creating the fluid chamber may have different shapes, including, but not limited to semi-circular, circular arc, square, rectangular, triangle, regular trapezoid, inverted trapezoid and etc. In one preferred embodiment, the cutout is in semi-circular shape. Obviously, the thickness and size of the cutout 41b determine the volume of the capillary chamber. Preferably, the first upper layer 400b has a thickness ranging from 0.01 mm to 0.5 mm, thus, the volume of the fluid chamber is about 0.1 to 5 microliter in the present invention.

Figure 7:
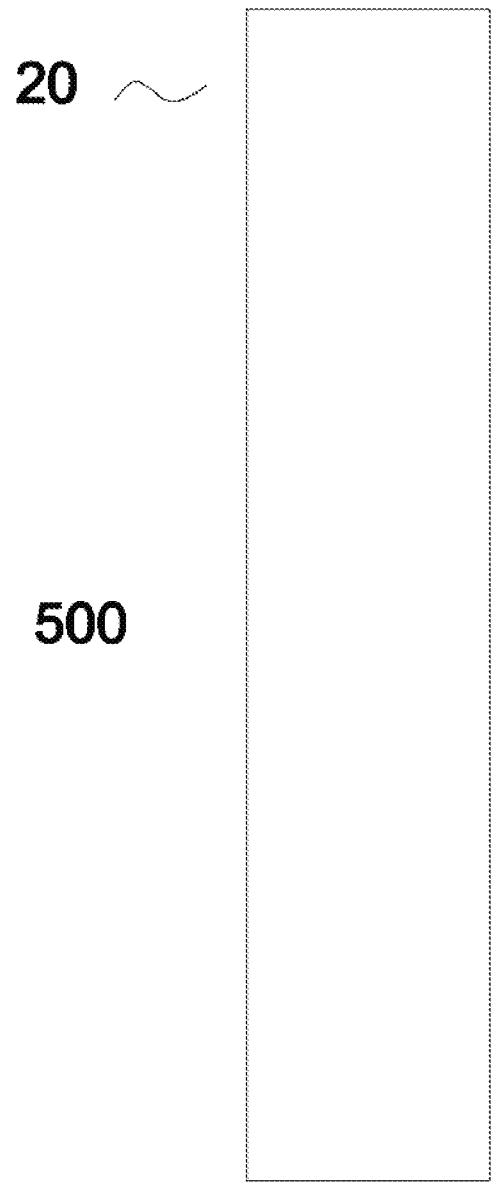
FIG. 7 is a top view of the second upper layer to be used in forming a test sensor according to one embodiment.

The laminated body may also have a second upper layer 500, as shown in FIG. 7, bonded to the first upper layer 400a or 400b, but without an additional vent opening, which is needed in convenient sensors. It virtually has the same width and length as the second base layer 300 or first base layer 400a in the first embodiment. While in the second embodiment, the second upper layer 500 may have the same width and length as the second base layer 300, thus, it is slightly longer than the first base layer 400b, such that side opening creates at the end 20. Still in the second embodiment, the second upper layer 500 may have the same width as the second base layer 300, but it can also have a length equal to or larger than the first upper layer 400b. The second upper layer 500 is made of a plastic or polymer materials. Non-limiting examples of polymeric materials, that may be used to form the second upper layer 500, include, but not limited to polyethylene, polyethylene terephthalate, polyethylene naphthalate, polyimide and combinations thereof. In one embodiment, the second upper layer 500 has a hydrophilic surface facing to the chamber to facilitate the capillary action. It should be understood that the entire side of the second upper layer 500 may be coated with a hydrophilic substance and then bonded to the first upper layer 400*a* or 400*b*. In the present invention, it is not critical to have an additional vent opening at the second upper layer 500.

Because of the unique design of the extra wide sampling entrance in the present invention, air escape is not an issue when a fluid sample such as blood enter the fluid chamber. Air can always find a way to escape from some part of the wide opening. Convenient test sensors always contain a vent opening for air escape when a fluid sample enters capillary channels. However, such vent opening may often cause problems, such as overflow, that may generate erratic test results. Besides, users may accidently apply blood sample to the vent opening instead of the normal blood sampling entrance, that may also compromise the test results. The test sensor of the present invention with combination of sampling entrance and air escape vent in one extra wide opening virtually eliminates such issues.

Figure 8:
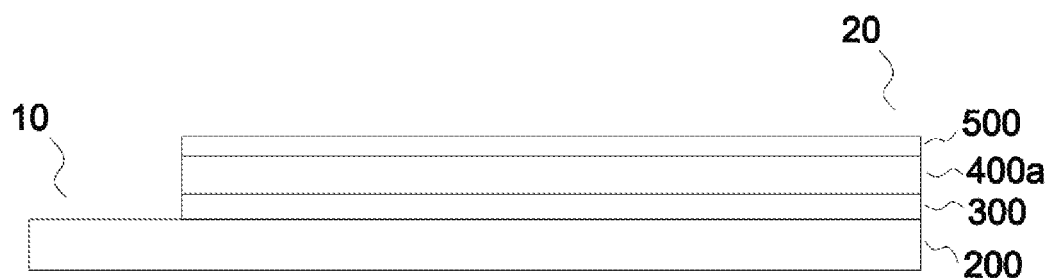
FIG. 8 is a side view of the test sensor according to the first embodiment of the present invention.

FIG. 8 shows side view of the test sensor of the first embodiment consisting of four laminated layers including a first base layer 200, second base layer 300, first upper layer 400*a* and second upper layer 500.

Figure 9:
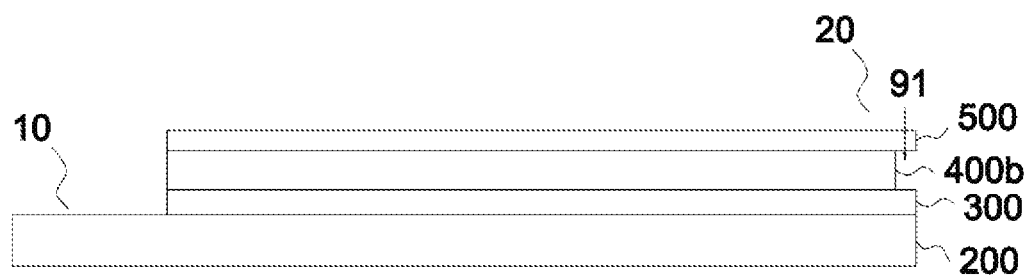
FIG. 9 is a side view of the test sensor according to the second embodiment of the present invention.

FIG. 9 shows side view of the test sensor of the second embodiment consisting of four laminated layers including a first base layer 200, second base layer 300, first upper layer 400*b* and second upper layer 500. Note 91 denotes the side opening described earlier. Obviously, its thickness is the same as the first upper layer 400. The length of the side opening 91 is preferably from 0.01 mm to 2.5 mm. More preferably, it is from 0.1 to 0.3 mm. Still more preferably, it is around 0.25 mm. It should be emphasized that the side opening 91 in the unique design of the present invention is just a part of the extra wide sampling opening. The side and front opening combine to form an over 180° sampling angle.

The advantage of the test sensor for blood sampling and air escape can be illustrated through FIGS. 10 and 11.

Figure 10A:
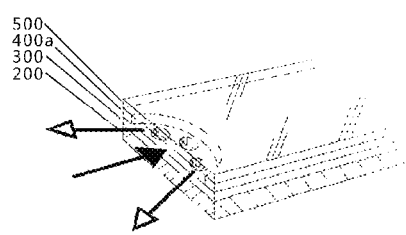
FIGS. 10a, 10b illustrate blood entering the fluid chamber and air escape for the test sensor according to the first embodiment of the present invention. Solid arrows and blank arrows denote blood sampling directions and air escape directions, respectively.
Figure 10B:
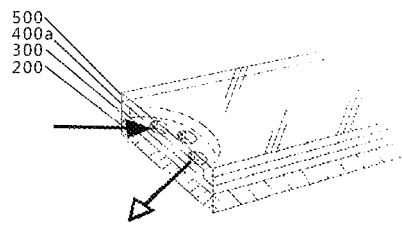

FIGS. 10*a*, 10*b* illustrate blood entering the fluid chamber and air escape for the test sensor according to the first embodiment of the present invention. Note solid arrows and blank arrows denote blood sampling directions and air escape directions, respectively. Because of the extra wide sampling entrance opening of the present invention, blood sample can enter the fluid chamber from any part of the front opening, while air escapes from the rest of the opening. For example, if blood sample enters from the middle of the opening, air can escape from both side of the front opening (FIG. 10*a*); if blood sample enters from one side of the front opening, air can escape from the other side (FIG. 10*b*).

Figure 11A:
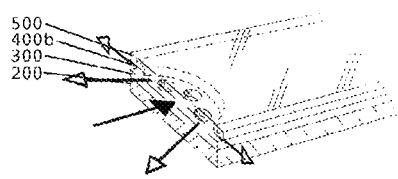
FIGS. 11a, 11b, 11c illustrate blood entering the fluid chamber and air escape for the test sensor according to the second embodiment of the present invention. Solid arrows and blank arrows denote blood sampling directions and air escape directions, respectively.
Figure 11B:
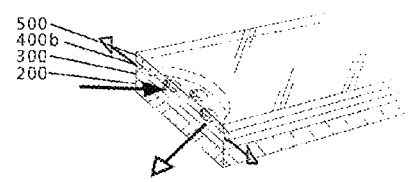
Figure 11C:
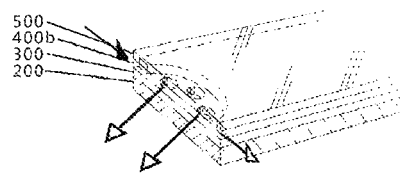

FIGS. 11*a*, 11*b*, 11*c* illustrate blood entering the fluid chamber and air escape for the test sensor according to the second embodiment of the present invention. Note solid arrows and blank arrows denote blood sampling directions and air escape directions, respectively. Because of the extra wide sampling entrance opening of the present invention, blood sample can enter the fluid chamber from any part of the over 180° opening, while air escapes from the rest of the opening. For example, if blood sample enters from the middle of the front opening, air can escape from both side of the front opening as well as from the side opening 91 (FIG. 11*a*); if blood sample enters from one side of the front opening, air can escape from the other side of the front opening as well as from the side opening 91 (FIG. 11*b*); if blood sample enters from one side opening 91, air can escape from the front opening as well as from the other side opening 91 (FIG. 11*c*).

Obviously, by having a test sensor with the extra wide openings in the first embodiment or second embodiment, being adapted to receive a fluid sample, the test sensor of the present invention more easily receives the fluid sample from a user and is more tolerant to users who jam the tip of the sensor into his/her finger, is more tolerant to fluid samples with very small volume (less than 1 microliter) and even smeared samples on the finger tip.

Referring back to FIGS. 1-3, the electrode cutouts 31, 32, 33 may be loaded with chemistries that react with an analyte to produce detectable electrochemical signals. The chemistries may contain an enzyme, an antibody, an antigen, a complexing reagent, a substrate or combination thereof. The reagents are selected to react with the desired analyte or analytes to be tested so as to assist in determining an analyte concentration of a fluid sample. In one embodiment, the reagents typically contain an enzyme such as, for example, glucose oxidase, glucose dehydrogenase, cholesterol oxidase, creatinine amidinohydrolase, lactate oxidase, peroxidase, uricase, xanthine oxidase and etc. which reacts with the analyte and with an electron acceptor such as a ferricyanide salt to produce an electrochemically measurable species that can be detected by the electrodes. For example, if the analyte of the test sensor is glucose, then glucose oxidase or glucose dehydrogenase may be included as the enzyme; if the analyte of the test sensor is uric acid, then uricase may be included as the enzyme. It should be noted that in some cases more than one enzyme may be included to construct the test sensor in order to generate detectable electrochemical signal. For example, in order to make a test sensor for cholesterol, cholesterol esterase, cholesterol oxidase and peroxidase may be included in the sensor.

In order for the test sensor works effectively, the electrode cutouts 31, 32, 33 may comprise a mixture of a polymer, an enzyme, a surfactant, an electron acceptor, an electron donor, a buffer, a stabilizer and a binder. The electrode cutouts 31, 32, 33 may further include a mediator that is an electron acceptor and assists in generating a current that corresponds to the analyte concentration. The preferable mediators could be redox chemicals either in oxidized or reduced form. The mediator used in the present invention may include, but not limited to various metal or noble metal complexes such as potassium ferricyanide, potassium ferrocyanide, cobalt phthalocyanine, various ferrocenes, and various organic redox mediators such as methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone, phenanthroline-5,6-dione and etc. For example, if the enzyme used to construct the test sensor is glucose oxidase or glucose dehydrogenase, then potassium ferricyanide may be included as redox mediator; if the enzyme used to construct the test sensor includes peroxidase, then potassium ferrocyanide may be included as redox mediator.

The electrode cutouts 31, 32, 33 include a first working electrode 31, a second working electrode 33 and a reference electrode 32. In one embodiment, the second working electrode 33 serves as a blank electrode without loading a chemistry that reacts with the analyte, such that background signal can be measured and be subtracted from the analyte signal resulted from the first working electrode 31. In this embodiment, effect of interference substances on the analyte signal could be minimized. Still in this embodiment, the electric signals such as current, impedance at the working electrodes 31 and 33, and time to obtain these signals could be used to estimate filling status of the fluid chamber (filled or not). Thus, this embodiment could alert under-fill of fluid samples.

Although the description of test sensor construction above describes construction for a single sensor, the design and materials used can also be used for making multiple sensors from one large piece of each layer material. This would be accomplished by starting with relative large pieces of the first base layer material, second base material, first upper layer material and second upper layer material. After a series of preparations described above, a plurality of multiple test sensors thus can be constructed to achieve mass production in a cost-effective way.

It should be noted that although the particular embodiments of the present invention have been described herein, the above description is merely for illustration purpose. Further modification and variations of the invention herein disclosed will occur to those skilled in the respective arts and all such modifications and variations are deemed to be within the scope of the invention as defined by the appended claims.

What is claimed is:

1. A sensor for sampling fluid samples comprising:
   a base layer, comprising three wells at a front end, the three wells in electric communication with an electric contact end of the base layer;
   a spacer attached to the base layer having a recessed portion on a front edge defining a fluid cavity, the fluid cavity constructed and arranged to be in fluid communication with the first, second, and third well of the base layer;
   an upper layer, the upper layer positioned above the spacer and defining a top of the fluid cavity, a fluid inlet formed along a front edge of the spacer providing fluid access to the fluid cavity and defined by front edges of the base layer and the upper layer;
   wherein the first well forms one of a reference electrode and a working electrode, and wherein the second and third wells are each the other of the reference or working electrode from the first well; and
   wherein the three wells are arranged to define an approximate triangle, the first well positioned at a vertex angle opposite to the triangle base which is defined by the second and third wells, the first well being farther from a front edge of the base layer than the second and third wells, the well arrangement providing accurate current so long as a fluid is contacting at least two of the three wells.

2. The sensor of claim 1 wherein the base layer is formed of a first base layer, and a second base layer, the second base layer defining the first, second, and third wells by forming an aperture through its thickness.

3. The sensor of claim 1 wherein the shape and dimensions of the fluid cavity facilitate the drawing of a fluid sample into the fluid cavity using a capillary action.

4. The sensor of claim 3 wherein the fluid inlet serves as an air escape vent to facilitate the fluid sample being drawn into the fluid cavity using the capillary action.

5. The sensor of claim 1 wherein the recessed portion of the spacer forms a semi-circular cross section of the fluid cavity.

6. The sensor of claim 1 wherein the first, second, and third well serve to hold a chemical selected to react with an analyte in a fluid sample to produce an electrochemical signal.

7. The sensor of claim 6 wherein the chemical is formed from substrates selected from the group consisting of: enzymes, antibodies, complexing reagents and combinations thereof.

8. The sensor of claim 6 wherein the chemical is formed from a mixture of a polymer, an enzyme, a surfactant, an electron acceptor, an electron donor, a buffer, a stabilizer and a binder.

9. The sensor of claim 6 wherein the chemical further comprises a mediator that is an electron acceptor, the mediator being redox chemicals either in oxidized or reduced form.

10. The sensor of claim 1 wherein the spacer is an electrically insulating material.

11. The sensor of claim 1 wherein the bottom surface of the upper layer is a hydrophilic surface.

12. The sensor of claim 1 wherein the recessed portion of the spacer is centrally disposed along the front edge of the spacer.

13. The sensor of claim 1 wherein the spacer is a double-sided adhesive tape.

14. The sensor of claim 1 wherein the front sampling end of the spacer is recessed from the front edge of the upper layer front sampling end and recessed from the front edge of the base layer front sampling end, the spacer recession defining two side openings, one on a first side of the test sensor and another on a second side of the test sensor.

15. The sensor of claim 14 wherein the two side openings are configured to allow a fluid to enter the fluid chamber through one of the two side openings when the first or second side of the test sensor is parallel to a surface that the fluid is on.

16. The sensor of claim 1 wherein the conductive coating is formed from materials selected from the group consisting of carbon, metals and metal oxides.

17. The sensor of claim 1 wherein the three wells are arranged to define an isosceles triangle.

18. A sensor for sampling fluid samples comprising:
   a base layer, comprising three wells at a front end, the three wells in electric communication with an electric contact end of the base layer;
   a spacer attached to the base layer having a recessed portion on a front edge defining a fluid cavity, the fluid cavity constructed and arranged to be in fluid communication with the first, second, and third well of the base layer;
   wherein the first well forms one of a reference electrode and a working electrode, and wherein the second and third wells are each the other of the reference or working electrode from the first well; and
   wherein the three wells are arranged to define an approximate triangle, the first well positioned at a vertex angle opposite to the triangle base which is defined by the second and third wells, the first well being farther from a front edge of the base layer than the second and third wells, the well arrangement providing accurate current so long as a fluid is contacting at least two of the three wells.

* * * * *